US012741996B2

(12) United States Patent
Chen

(10) Patent No.: US 12,741,996 B2
(45) Date of Patent: Sep. 22, 2026

(54) MODULATION OF Wnt5a TO TREAT GLAUCOMA

(71) Applicant: The Regents of the University of California, Oakland, CA (US)

(72) Inventor: Lu Chen, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/522,141

(22) Filed: Nov. 28, 2023

(65) Prior Publication Data

US 2024/0124538 A1 Apr. 18, 2024

Related U.S. Application Data

(63) Continuation of application No. 16/752,677, filed on Jan. 26, 2020, now abandoned, which is a continuation of application No. PCT/US2018/046578, filed on Aug. 14, 2018.

(60) Provisional application No. 62/547,854, filed on Aug. 20, 2017.

(51) Int. Cl.

| | |
|---|---|
| ***C07K 14/47*** | (2006.01) |
| ***A61K 9/06*** | (2006.01) |
| ***A61K 31/335*** | (2006.01) |
| ***A61P 27/06*** | (2006.01) |
| ***C07K 7/06*** | (2006.01) |
| ***C07K 16/22*** | (2006.01) |
| ***C12N 15/11*** | (2006.01) |
| *A61K 9/00* | (2006.01) |
| *A61K 38/00* | (2006.01) |
| *A61K 39/00* | (2006.01) |

(52) U.S. Cl.

CPC ........ *C07K 14/4703* (2013.01); *A61K 9/0048* (2013.01); *A61K 9/06* (2013.01); *A61K 31/335* (2013.01); *A61P 27/06* (2018.01); *C07K 7/06* (2013.01); *C07K 16/22* (2013.01); *C12N 15/111* (2013.01); *A61K 9/0019* (2013.01); *A61K 38/00* (2013.01); *A61K 2039/505* (2013.01); *A61K 2039/54* (2013.01)

(58) Field of Classification Search

CPC ... C12N 15/111; C12N 15/113; A61K 9/0019; A61K 9/0048; A61K 48/00; A61K 2309/505

See application file for complete search history.

(56) References Cited

U.S. PATENT DOCUMENTS

| | | | |
|---|---|---|---|
| 9,573,998 | B2 | 2/2017 | Gurney et al. |
| 10,550,113 | B2 | 2/2020 | Mellstedt et al. |
| 2009/0226425 | A1 | 9/2009 | Clark |
| 2010/0137201 | A1 | 6/2010 | Ferguson et al. |
| 2012/0101074 | A1 | 4/2012 | Lam et al. |
| 2013/0058954 | A1 | 3/2013 | Sutton |
| 2013/0131139 | A1 | 5/2013 | Tyner |
| 2014/0199277 | A1 | 7/2014 | Cosma et al. |
| 2015/0307882 | A1 | 10/2015 | Clark et al. |
| 2015/0328262 | A1 | 11/2015 | Klassen et al. |
| 2017/0073681 | A1 | 3/2017 | Clark |
| 2018/0002329 | A1 | 1/2018 | Mellstedt et al. |
| 2018/0112002 | A1 | 4/2018 | Kipps et al. |
| 2018/0312838 | A1 | 11/2018 | Chen et al. |
| 2019/0376065 | A1* | 12/2019 | Humphries ............. A61P 27/06 |
| 2020/0157158 | A1 | 5/2020 | Chen |
| 2021/0363247 | A1 | 11/2021 | Chen et al. |

FOREIGN PATENT DOCUMENTS

| | | | |
|---|---|---|---|
| CN | 101117644 | A | 2/2008 |
| CN | 101511383 | A | 8/2009 |
| KR | 20090004272 | A | 1/2009 |
| WO | WO2003/086334 | A1 | 8/2005 |
| WO | 2015/200920 | A1 | 12/2015 |
| WO | WO 2016092378 | A1 | 6/2016 |
| WO | 2016/172726 | A1 | 10/2016 |
| WO | 2019/040311 | A1 | 2/2019 |
| WO | 2020/160197 | A1 | 8/2020 |

OTHER PUBLICATIONS

Andres-Guerrero V., et al., "Targeting Schlemm's Canal in the Medical Therapy of Glaucoma: Current and Future Considerations," *Adv Ther*. May 1, 2017, 34, 5, 1049-1069.

Becker, B., "Intraocular Pressure Response to Topical Corticosteroids," *Invest Ophthalmol*. Apr. 1965, 4, 198-205.

Billiard, J., et al., "The orphan receptor tyrosine kinase Ror2 modulates canonical Wnt signaling in osteoblastic cells," *Molecular Endocrinology*, 2005, 19, 1, 90-101.

Borrás, T., et al., "First look at the effect of overexpression of TIGR/MYOC on the transcriptome of the human trabecular meshwork," *Exp. Eye Res*. 2006, 82, 6, 1002-1010.

Bull, H., et al., "Three-year canaloplasty outcomes for the treatment of open-angle glaucoma: European study results," *Graefes Arch Clin Exp Ophthalmol*. Jul. 6, 2011, 249, 10, 1537-1545.

Fujimura, N., "WNT/β-Catenin Signaling in Vertebrate Eye Development," *Front Cell Dev Biol*. Nov. 30, 2016, 4, 138.

Grumolato, L., et al., "Canonical and noncanonical Wnts use a common mechanism to activate completely unrelated coreceptors," *Genes Dev*. Nov. 15, 2010, 24, 22, 2517-2530.

Huang, X., et al., "Genome editing abrogates angiogenesis in vivo," *Nat Commun*. Jul. 24, 2017, 8, 1, 112.

Johnson, M.C., and Kamm, R.D., "The role of Schlemm's canal in aqueous outflow from the human eye," *Invest Ophthalmol Vis Sci*. Mar. 1983, 24, 3, 320-325.

Kamizaki, K., et al., "Ror2 signaling regulated by differential Wnt proteins determines pathological fate of muscle mesenchymal progenitors," *Cell Death and Disease*, 2024, 15, 784.

Keller, K. E., et al., "Consensus recommendations for trabecular meshwork cell isolation, characterization and culture," *Experimental Eye Research*, 2018, 171, 164-173.

(Continued)

*Primary Examiner* — J. E. Angell

(74) *Attorney, Agent, or Firm* — Richard Aron Osman

(57) ABSTRACT

Glaucoma or pathogenic intraocular pressure is treated by locally administering to an eye in need thereof formulations of a Wnt5a inhibitor.

23 Claims, No Drawings

(56) References Cited

OTHER PUBLICATIONS

Mäepea, O., and Bill, A., "Pressures in the juxtacanalicular tissue and Schlemm's canal in monkeys," *Exp Eye Res*. Jun. 1992, 54, 6, 879-883.
Mcdonald, S.L., and Silver, A., "The opposing roles of Wnt-5a in cancer," *Br J Cancer*, Jul. 14, 2009, 101, 209-214.
Overby, D. R., et al., "Animal models of glucocorticoid-induced glaucoma," *Experimental Eye Research*, 2015, 141, 15-22.
Pereira, C., et al., "Wnt5A/CaMKII Signaling Contributes to the Inflammatory Response of Macrophages and Is a Target for the Antiinflammatory Action of Activated Protein C and Interleukin-10," *Arterioscler Thromb Basc Biol*, Jan. 3, 2008, 28, 504-510.
Sessa, R., et al., "Monocyte-derived Wnt5a regulates inflammatory lymphangiogenesis," *Cell Res*. Feb. 2016, 26(2):262-265.
Stamer, D. W., et al., "The many faces of the trabecular meshwork cell," *Exp Eye Res*. May 2017, 158, 112-123.
Sugali, C. K., et al., "The Canonical Wnt Signaling Pathway Inhibits the Glucocorticoid Receptor Signaling Pathway in the Trabecular Meshwork," *The American Journal of Pathology*, 2021, 191, 6, 1020-1035.
Tian, A., et. al, "To be or not to be—Decoding the Trabecular Meshwork Cell Identity," *bioRxiv*, Apr. 29, 2024, doi: https://doi.org/10.1101/2024.04.26.591346.
Truong, T.N. et al, "Novel characterization and live imaging of Schlemm's canal expressing Prox-1," *PLoS One*, May 14, 2014, 9, 5, e98245.
Weinreb, R. N., et al., "The pathophysiology and treatment of glaucoma: a review," *JAMA*, May 14, 2014, 311, 18, 1901-1911.
Weissenböck, M., et al., "Genetic interactions between Ror2 and Wnt9a, Ror1 and Wnt9a and Ror2 and Ror1: Phenotypic analysis of the limb skeleton and palate in compound mutants," *Genes Cells*. Apr. 2019; 24, 4, 307-317.
Yuan, Y. et al., "Transient expression of Wnt5a elicits ocular features of pseudoexfoliation syndrome in mice," *PLoS One*, Mar. 6, 2019, 14, 3, e0212569.
Zhang, L. et al., "Establishment and Characterization of an Acute Model of Ocular Hypertension by Laser-Induced Occlusion of Episcleral Veins," *Invest Ophthalmol Vis Sci*. Aug. 1, 2017, 58, 10, 3879-3886.
Ahadome, S.D. et al. Small-molecule inhibition of Wnt signaling abrogates dexamethasone induced phenotype of primary human trabecular meshwork cells. Exp Cell Res. 357(1):116-123(Aug. 1, 2017).
Anastas, J.N. et al. WNT5A enhances resistance of melanoma cells to targeted BRAF inhibitors. J Clin Investig. 124:2877-2890(2014).
Bhatt, P. et al. Wnt5a: A player in the pathogenesis of atherosclerosis and other inflammatory disorders. Atherosclerosis. 237(1):155-162(Sep. 3, 2014).
Edwards, B.M. et al. The remarkable flexibility of the human antibody repertoire; isolation of over one thousand different antibodies to a single protein, BlyS. Journal of Molecular Biology. 334(1):103-118(Nov. 14, 2003).
Extended European Search Report (Jul. 24, 2020). EP18847365.6.
Gote, V. et al. Ocular Drug Delivery: Present Innovations and Future Challenges. J Pharmacol and Exp Therapeutics. 370(3):602-624(Sep. 2019).
Hanaki, H. et al. An Anti-Wnt5a Antibody Suppresses Metastasis of Gastric Cancer Cells In Vivo by Inhibiting Receptor-Mediated Endocytosis. Mol Cancer Ther. 11(2):298-307(Feb. 2012).
Hanaki, H. et al. An Anti-Wnt5a Antibody Suppresses Metastasis of Gastric Cancer Cells In Vivo by Inhibiting Receptor-Mediated Endocytosis. Mol Cancer Ther. 11(2):298-307(Feb. 2012). Supplementary Data, pp. 1-17.
He, B. et al. Blockade of Wnt-1 signaling induces apoptosis in human colorectal cancer cells containing downstream mutations. Oncogene. 24:3054-3058(2005).
International Search Report & Written Opinion (Feb. 29, 2019). PCT/US2018/046578, WO2019040311.
Jenei, V. et al. A t-butyloxycarbonyl-modified Wnt5a-derived hexapeptide functions as a potent antagonist of Wnt5a-dependent melanoma cell invasion. PNAS. 106(46):19473-19478(Nov. 17, 2009).
Kim, T.W. et al. Biphasic activation of WNT signaling facilitates the derivation of midbrain dopamine neurons from hESCs for translational use. Cell Stem Cell. 28(2):343-355.e5(Feb. 4, 2021).
Mandal, A. et al. Ocular delivery of proteins and peptides: Challenges and novel formulation approaches. Adv Drug Deliv Rev. 126:67-95(Feb. 15, 2018).
Martinez, T. et al. In Vitro and In Vivo Efficacy of SYL040012, a Novel siRNA Compound for Treatment of Glaucoma. Mol Ther. 22(1):81-91(Jan. 2014).
Morgan, J.T. et al. Wnt inhibition induces persistent increases in intrinsic stiffness of human trabecular meshwork cells. Exp Eye Res. 132:174-178(Mar. 2015).
Shinonaga, H. et al. Synthesis and structure-activity relationships of radicicol derivatives and WNT-5A expression inhibitory activity. Bioorganic & Medicinal Chem. 17:4622-4635(2009).
Tam, L.C.S. et al. Enhancement of Outflow Facility in the Murine Eye by Targeting Selected Tight-Junctions of Schlemm's Canal Endothelia. Sci Rep. 7:40717(Jan. 16, 2017).
Uneo, S. et al. Biphasic role for Wnt/-catenin signaling in cardiac specification in zebrafish and embryonic stem cells. PNAS. 104(23):9685-9690(Jun. 5, 2007).
Wang, W-H. et al. Increased expression of the WNT antagonist sFRP-1 in glaucoma elevates intraocular pressure. J Clin Invest. 118(3):1056-1064(2008).
Yuan, Y. et al. Dexamethasone Induces Cross-Linked Actin Networks in Trabecular Meshwork Cells Through Noncanonical Wnt Signaling. Investigative Ophthalmology & Visual Science. Invest Ophthalmol Vis Sci. 54(1):6502-6509(Oct. 3, 2013).
Yuan, Y. et al. Activation of Noncanonical Wnt Signaling Elicits Glaucoma in Mice. Investigative Ophthalmology & Visual Science. 56(7):3677(Jun. 2015).
Yuen, D. et al. Role of Angiopoietin-2 in Corneal Lymphangiogenesis. Invest Ophthalmol Vis Sci. 55:3320-3327(Apr. 29, 2014).
Gray, J.D. et al. (Nov. 1, 2013, e-pub. Jun. 16, 2013). "LRP6 Exerts Non-canonical Effects on Wnt Signaling During Neural Tube Closure," Human Molecular Genetics. 22(21):4267-4281.
Liu, C. et al. (Apr. 1, 2016, e-pub. Jan. 24, 2016). "A Secreted WNT-ligand-binding Domain of FZD5 Generated by a Frameshift Mutation Causes Autosomal Dominant Coloboma," Hum Mol Genet. 25(7):1382-1391.
Sen, M. et al. (Apr. 2001). "Blockade of Wnt-5A/Frizzled 5 Signaling Inhibits Rheumatoid Synoviocyte Activation," Arthritis Rheum. 44(4):772-781.
Steinhart, Z. et al. (Jan. 2017, e-pub. Nov. 21, 2016). "Genome-wide CRISPR Screens Reveal a Wnt-FZD5 Signaling Circuit as a Druggable Vulnerability of RNF43-mutant Pancreatic Tumors" Nat Med. 23(1):60-68.
Thermo Fisher Scientific. "Rat1, Rat Fibroblast Cells" located at <https://www.thermofisher.com/us/en/home/technical-resources/cell-lines/r/cell-lines-detail-373.html>, last visited on Jan. 16, 2026, 1 page.
Yu, J. et al. (Feb. 2016 ). "Wnt5a Induces ROR1/ROR2 Heterooligomerization to Enhance Leukemia Chemotaxis and Proliferation," J Clin Invest. 126(2):585-598.
Zhang, K. et al. (Jul. 2012, e-pub. Jun. 15, 2012 ). "Ophthalmic Drug Discovery: Novel Targets and Mechanisms for Retinal Diseases and Glaucoma," Nature Reviews Drug Discovery 11(7):541-559.

* cited by examiner

MODULATION OF Wnt5a TO TREAT GLAUCOMA

CROSS-REFERENCE TO RELATED APPLICATIONS

This application is a continuation of Ser. No. 16/752,677, filed: Jan. 26, 2020, which is a continuation of PCT/US18/46578, filed Aug. 14, 2018, which claims the benefit of Ser. 62/547,854, filed: Aug. 20, 2017, the contents of each of which are incorporated herein by reference in their entirety.

STATEMENT REGARDING FEDERALLY SPONSORED RESEARCH

This invention was made with government support under Grant Numbers EY017392 and EY028995 awarded by the National Institutes of Health. The government has certain rights in the invention.

INTRODUCTION

Glaucoma is a major health problem which affects over 3 million Americans and 60 million people worldwide. It is estimated that 111.8 million people will be affected by this disease worldwide in 2040. A major risk factor for this disease is increased intraocular pressure (IOP), which can damage the optic nerve and cause permanent blindness without treatment. Currently, there is no cure for glaucoma. Existing eye drops or oral medications are of limited efficacy with many side effects, and surgeries often fail with scar formation and fibrosis.

Aqueous humor is the clear colorless liquid that fills the anterior and posterior chambers of the eye. It is produced by the ciliary body at the posterior chamber and exits the anterior chamber angle through the conventional pathway via trabecular meshwork and Schlemm's canal, and the nonconventional pathway via uveoscleral outflow. In normal eyes, a dynamic balance exists between the production and drainage of aqueous humor, maintaining IOP in the normal range.

Schlemm's canal (SC) is a circumferential channel located at the iridocorneal angle in the ocular anterior chamber. It is part of the conventional aqueous humor outflow system, which accounts for 70-90% of the total aqueous humor that drains out of the eye in human. The endothelial cell lining of Schlemm's canal is one of the primary sites of resistance to aqueous humor drainage and is a major determinant of IOP. When canal resistance increases with age or under pathological situation, IOP is elevated leading to glaucoma with irreversible optic nerve damage and vision loss. It is therefore an important target for glaucoma therapy. Recently, we provided the first evidence that Schlemm's canal expresses Prox-1, the master control gene of lymphatic formation (Truong T N, Li H, Hong Y K, Chen L. Novel characterization and live imaging of Schlemm's canal expressing Prox-1. PLoS One. 2014; 9(5): e98245).

Wnt5a belongs to the Wnt family that comprises ligands and receptors in mammals.

Here we disclose that Wnt5a is expressed on Schlemm's canal, and its expression is regulated in response to sheer stress change. Moreover, by inhitingWnt5a, we can effectively lower IOP in vivo.

SUMMARY OF THE INVENTION

The invention provides methods and compositions for locally treating glaucoma or pathogenic intraocular pressure.

In an aspect the invention provides a method of treating glaucoma or pathogenic intraocular pressure, comprising locally administering to an eye in need thereof a Wnt5a inhibitor.

In embodiments:

- the administering step comprises delivery by eye drop or by intracameral, subconjunctival injection, or intravitreal injection;
- the inhibitor is selected from an antibody, an siRNA, an small interfering peptide, and a small molecule inhibitor;
- the inhibitor is delivered by viral vector, such as AAV or lentivirus; and/or
- the administration is topical, and the inhibitor is administered in form of a topical ophthalmic gel, ointment, suspension or solution;

In another aspect, the invention provides an ophthalmic formulation of a Wnt5a-specific inhibitor selected from an antibody, an siRNA, an small interfering peptide, and a small molecule inhibitor, in unit dosage form for treating glaucoma or pathogenic intraocular pressure.

In embodiments:

- the formulation is in the form of a topical ophthalmic gel, ointment, suspension or solution, such as an ophthalmic lubricant;
- the dosage form is an inhibitor-loaded contact lens, eye drop, depot or bollus
- the formulation is packaged in an eye drop dispenser;
- the formulation is loaded in a syringe configured for intracameral injection, subconjunctival injection or intravitreal injection; and/or
- the formulation further comprises excipients and/or features suitable for direct, topical delivery to the eye, such as selected from the group consisting of ophthalmically suitable clarity, pH buffer, tonicity, viscosity, stability and sterility.

The invention encompasses all combinations of the particular embodiments recited herein. The methods may be practiced with all disclosed compositions including specific embodiments.

DESCRIPTION OF PARTICULAR EMBODIMENTS OF THE INVENTION

The examples and embodiments described herein are for illustrative purposes and various modifications or changes in light thereof will be apparent to persons skilled in the art and are to be included within this invention. Those skilled in the art will recognize a variety of noncritical parameters that could be changed or modified to yield essentially similar results. The invention may exclude or be practiced in the absence of any compound, component, element or step which is not disclosed are required herein. Unless contraindicated or noted otherwise, in these descriptions and throughout this specification, the terms "a" and "an" mean one or more. All publications, patents, and patent applications cited herein, including citations therein, are hereby incorporated by reference in their entirety for all purposes.

The disclosed Wnt5a inhibition methods can be genetic manipulation, and/or administrations of small interfering RNAs (siRNAs), antibodies, small molecules, etc., many of which are commercially available from sources like Applied Biological Materials Inc. (ABM, Richmond BC), Life Technologies (ThermoFisher Scientific), Sigma-Aldrich, etc. The methods can be used alone to lower intraocular pressure and to prevent or treat glaucoma, and/or in combination with other therapeutic approaches, such as eye drops, medications, laser, implanted devices, and surgery, etc. to prevent or treat glaucoma.

Prototypical Examples

Wnt5a is expressed on human primary SC cells in culture and mouse SC in vivo. Wnt5a expression is regulated with sheer stress change, as analyzed by quantitative real-time PCR assay. We also demonstrate that Wnt5a expression in human SC cells can be down-regulated by Wnt5a-specific siRNA, which affects SC cell functions as well. In SC-specific Wnt5a gene conditional knockout mice IOP elevation induced in a glaucoma model is significantly reduced compared to control littermates. No significant difference was found in baseline IOP between the knockout mice and control littermates. Compared with the control littermates that had IOP elevation at all time-points studied, Wnt5a knockout mice only showed elevated IOP at the early (within 24 hours) but not later time points, indicating an unsustainable IOP increase with Wnt5a intervention. We also demonstrate that wnt5a intervention is effective in protecting retinal nerve fiber layer and increasing SC permeability, a target for enhancement of aqueous movement through the conventional outflow system to manage ocular hypertension (e.g. Tam et al., Scientific Reports 7:40717, DOI: 10.1038/srep40717). These experiments demonstrate Wnt5a is an effective therapeutic target for glaucoma management. These results are further demonstrated by selective inhibition of Wnt5a by CRISPR gene editing employing the methods of Huang, et al. (Nature Communications, 2017; 8 (1) DOI: 10.1038/s41467-017-00140-3).

We next developed experimental protocols to demonstrate efficacy of Wnt5a siRNA inhibitor treatments to reduce IOP. For these protocols Wnt5a specific siRNA was obtained commercially (human WNT5A siRNA, Life Technologies; Anastas, et al. J. Clin. Investig. 2014, 124, 2877-2890). In one protocol subconjuctival injection of siRNA is performed as described by Yuen et al. (2014, Invest Ophthalmol Vis Sci. 2014; 55:3320-3327). Mice are randomly selected to receive subconjunctival injection of 5 uL (0.2 lg/uL) siRNA or control twice a week for 2 weeks. In a second protocol intracameral injection of siRNA is performed as described by Tam et al. (2017, Scientific Reports 7, 40717). Mice are anaesthetized by intra-peritoneal injection, and pupils are dilated. A pulled blunt-ended micro-glass needle is first used to puncture the cornea to withdraw aqueous humour Immediately after puncture, a pulled blunt-ended micro-glass needle attached to a 10 μl syringe is inserted through the puncture, and 1.5 μl of PBS containing 1 μg siRNA is administered into the anterior chamber. Contralateral eyes receive an identical injection of 1.5 μl containing the same concentration of scrambled siRNA. These experiments demonstrate that Wnt5a-specific inhibitor siRNA delivered locally by either subconjuctival injection or intracameral injection is an effective therapy for pathogenic IOP.

To assess the effect of siRNA delivered by eye drops on IOP, we developed an additional protocol based on the methods of Martinez et al. (Mol Ther. 2014 January; 22(1): 81-91), wherein New Zealand White rabbits receive a topical administration of either 20 nmol/day of siRNA or phosphate-buffered saline (PBS) over a period of 4 consecutive days. Treated eyes present a significant IOP decrease when compared with the vehicle-treated group. The effect of the siRNA on IOP is detectable 2 days after the first administration and values remains below basal levels until ~2 days after the last administration. We also adapted an oral water overloading model in New Zealand White Rabbits to evaluate the IOP-lowering effect of Wnt5a siRNA in pathologic conditions like observed in glaucoma. Initially four different doses of siRNA (10 nmol, 20 nmol, 40 nmol, and 60 nmol/eye/day) are administered a total of three times: 48, 24, and 2 hours before hypertension induction. All treatments are applied in both eyes and IOP measured before hypertension induction and every 20 minutes up to 120 minutes after oral overloading. Analysis of the results shows that the Wnt5a siRNA provides significant protection against the rise of IOP at all doses tested.

To confirm the efficacy and specificity of Wnt5a siRNA on IOP, a larger group of animals is treated with a dose of 40 nmol/eye/day over a period of 4 consecutive days; on the fourth day, ocular hypertension is induced by water loading. Control results demonstrate that water loading caused an increase in IOP during the first hour after hypertension induction in animals treated with PBS. Analysis performed by comparing IOP values at each time point indicate that treatment with siRNA significantly reduced ΔIOP values within the first hour compared with PBS-treated animals. The effect is specific since treatment with a scrambled sequence siRNA has no effect on IOP.

We next developed experimental protocols to demonstrate efficacy of Wnt5a specific antibody inhibitor treatments to reduce IOP. These protocols employ two different antibodies: anti-human WNT5A antibody produced in rabbit purified immunoglobulin, buffered aqueous solution (Sigma-Aldrich SAB1411396), and an anti-human WNT5A monoclonal antibody produced in mouse clone 6F2, ascites fluid (Sigma-Aldrich SAB5300183), although other Wnt5a antibodies can be used, e.g. Hanaki et al., Mol Cancer Ther 11(2) February 2012; He et al. Oncogene. 2005, 24 (18): 3054-3058. Using both the mouse and rabbit models (supra), these experiments demonstrate that Wnt5a-specific antibody inhibitor delivered locally by eye drops is an effective therapy for pathogenic IOP.

In an exemplary model system intraocular hypertension was induced in the right eye (OD) of wildtype normal mice and Wnt5a neutralizing antibodies were administered to assess their therapeutic effects on IOP and other parameters of glaucoma including corneal edema, retinal ganglion cell (RGC) death, and RNFL thinning Compared to the control group where IOP was significantly elevated in the right eyes of the mice, IOP in Wnt5a antibody treated eyes was significantly lower and maintained at the baseline level. Wnt5a intervention reduced corneal edema, as measured by central corneal thickness in vivo by OCT. Increased corneal thickness was observed in the control group after IOP was increased, but not in Wnt5a antibody treated eyes. Wnt5a intervention reduced RGC death as well as RNFL thinning in the treated eyes. These were detected by immunostaining and OCT, respectively. These results confirmed that topical Wnt5a antibody intervention significantly lowers IOP and protects the cornea and retina in a mouse model of glaucoma.

We next designed experimental protocols to demonstrate efficacy of Wnt5a specific antagonist peptide and small molecule inhibitor treatments to reduce IOP. These protocols employ a t-butyloxycarbonyl-modified Wnt5a-derived hexapeptide (Boxy) that functions as a potent antagonist of Wnt5a (Jenei, et la., PNAS USA, 106 (46), 19473-8), and 6,7-dihydro-10alpha-hydroxy radicicol, a potent WNT-5A expression inhibitor with relatively low toxicity and excellent stability (Shinonaga et al. Bioorg Med Chem. 2009 Jul. 1; 17(13):4622-35). Again using both the mouse and rabbit models (supra), these experiments demonstrate that Wnt5a-specific modified peptide inhibitor and small molecule inhibitor of Wnt5a expression, delivered locally by eye drops are effective therapies for pathogenic IOP.

The invention claimed is:

1. A method of treating glaucoma or pathogenic intraocular pressure (IOP) comprising locally administering to an eye in need thereof a Wnt5a inhibitor, wherein the Wnt5a inhibitor is a neutralizing antibody against Wnt5a or a small interfering ribonucleic acid (siRNA) that targets Wnt5a-encoding nucleic acids.

2. The method of claim 1, wherein the Wnt5a inhibitor is a neutralizing antibody against Wnt5a.

3. The method of claim 1, wherein the Wnt5a inhibitor is an siRNA that targets Wnt5a-encoding nucleic acids.

4. The method of claim 1, wherein the Wnt5a inhibitor is administered by eye drop or an injection selected from an intracameral injection, a subconjunctival injection, or an intravitreal injection.

5. The method of claim 4, wherein the Wnt5a inhibitor is administered by eye drop.

6. The method of claim 4, wherein the Wnt5a inhibitor is administered by subconjunctival injection.

7. The method of claim 4, wherein the Wnt5a inhibitor is administered by intracameral injection.

8. The method of claim 4, wherein the Wnt5a inhibitor is administered by intravitreal injection.

9. The method of claim 1, which results in one or more therapeutic effects, wherein the one or more therapeutic effects are reduced intraocular pressure (IOP), increased Schlemm's canal permeability, reduced corneal edema, maintained corneal thickness, reduced retinal ganglion cell (RGC) death, reduced retinal nerve fiber layer (RNFL) thinning, or a combination thereof.

10. The method of claim 1, further comprising administering at least one additional therapeutic approach, wherein the at least one additional therapeutic approach is an eye drop therapy, medication therapy, laser therapy, implanted device therapy, or surgery.

11. The method of claim 1, further comprising detecting a resultant one or more therapeutic effects, wherein the resultant one or more therapeutic effects are reduced IOP, increased Schlemm's canal permeability, reduced corneal edema, maintained corneal thickness, reduced retinal ganglion cell (RGC) death, reduced retinal nerve fiber layer (RNFL) thinning, or a combination thereof.

12. The method of claim 3, wherein the Wnt5a-encoding nucleic acids are human Wnt5a-encoding nucleic acids.

13. The method of claim 12, wherein the Wnt5a inhibitor is administered by eye drop or injection, wherein the injection is intracameral injection, subconjunctival injection, or intravitreal injection.

14. The method of claim 12, wherein the Wnt5a inhibitor is administered by eye drop.

15. The method of claim 12, wherein the Wnt5a inhibitor is administered by subconjunctival injection.

16. The method of claim 12, wherein the Wnt5a inhibitor is administered by intracameral injection.

17. The method of claim 12, wherein the Wnt5a inhibitor is administered by intravitreal injection.

18. The method of claim 12, further comprising of detecting a resultant reduced IOP.

19. The method of claim 13, further comprising of detecting a resultant reduced IOP.

20. The method of claim 14, further comprising of detecting a resultant reduced IOP.

21. The method of claim 15, further comprising detecting a resultant reduced IOP.

22. The method of claim 16, further comprising detecting a resultant reduced IOP.

23. The method of claim 17, further comprising detecting a resultant reduced IOP.

* * * * *